United States Patent
Chen

(12) 
(10) Patent No.: US 8,386,003 B2
(45) Date of Patent: Feb. 26, 2013

(54) PORTABLE MEDICAL DEVICE

(75) Inventor: Kun-Sung Chen, Hsi-Chih (TW)

(73) Assignee: Digio2 International Co., Ltd., Miaoli Hsien (TW)

( * ) Notice: Subject to any disclaimer, the term of this patent is extended or adjusted under 35 U.S.C. 154(b) by 440 days.

(21) Appl. No.: 12/774,167

(22) Filed: May 5, 2010

(65) Prior Publication Data

US 2011/0275906 A1 Nov. 10, 2011

(51) Int. Cl.
*A61B 5/00* (2006.01)
*A61B 5/04* (2006.01)

(52) U.S. Cl. ......................... 600/344; 600/386

(58) Field of Classification Search .................. 600/300, 600/323, 344, 386, 388, 390
See application file for complete search history.

(56) References Cited

U.S. PATENT DOCUMENTS

| | | | | |
|---|---|---|---|---|
| 4,809,700 A | * | 3/1989 | Castelli | 600/384 |
| 6,198,951 B1 | * | 3/2001 | Kosuda et al. | 600/323 |
| 6,529,754 B2 | * | 3/2003 | Kondo | 600/344 |
| 6,850,788 B2 | * | 2/2005 | Al-Ali | 600/323 |
| 7,060,963 B2 | * | 6/2006 | Maegawa et al. | 250/221 |
| 7,280,860 B2 | * | 10/2007 | Ikeda et al. | 600/344 |
| 2002/0095092 A1 | * | 7/2002 | Kondo et al. | 600/503 |
| 2005/0234351 A1 | * | 10/2005 | Nishii et al. | 600/503 |
| 2008/0021290 A1 | * | 1/2008 | Sawa et al. | 600/300 |
| 2008/0171915 A1 | * | 7/2008 | Kawajiri et al. | 600/300 |

* cited by examiner

*Primary Examiner* — W. B. Perkey
(74) *Attorney, Agent, or Firm* — Rabin & Berdo, P.C.

(57) ABSTRACT

A portable medical device has a medical measuring apparatus and an elastic mounting portion. The medical measuring apparatus has a body. The body has a mounting mechanism. The elastic mounting portion is arched, adapted to be mounted around a subject's wrist or arm and has two edges and an attaching mechanism. The two edges are opposite to each other and define a gap for placement of the subject's wrist or arm. The attaching mechanism detachably engages the mounting mechanism of the body of the medical measuring apparatus. Thus the portable medical device is convenient for daily use and for carrying on a subject by simply mounting around the subject's wrist or arm by the elastic mounting portion.

10 Claims, 5 Drawing Sheets

US 8,386,003 B2

PORTABLE MEDICAL DEVICE

BACKGROUND OF THE INVENTION

1. Field of the Invention

The present invention relates to a portable medical device for monitoring physical parameters, particularly to a wrist-carriable medical device for home health monitoring.

2. Description of the Prior Arts

Medical monitors allow medical staff to measure a patient's medical state. Medical monitors may measure patient vital signs and other parameters including blood pressure, dissolved gases in the blood and electrocardiography (ECG). Portable medical devices for home health monitoring, such as ambulatory blood pressure monitors, electronic sphygmomanometers, fingertip pulse oximeters and the like are usually made as handheld products without a fastening structure to be held on the patient. At most, a conventional portable medical device, particularly an electronic sphygmomanometer, has a band for attaching around an arm using hook and loop fasteners. However, for use a patient's arm is inserted through the band, tightened and the hook and loop fastener fastened. Tightening or loosening the fastener with one hand and holding the portable medical device with another hand is inconvenient and confusion may cause the device to be dropped. Therefore, the conventional portable medical device is not convenient for patients to operate by themselves and medical staff are required to aid use.

Indeed, there is a need for a portable medical device with an improved structure for detachable attachment to a subject requiring the portable medical device in the art.

To overcome the shortcomings and satisfy the need, the present invention provides a portable medical device to mitigate or obviate the aforementioned problems.

SUMMARY OF THE INVENTION

The main objective is to provide a portable medical device capable of being fixed on a subject with simplified steps for convenience of daily use by patients or medical staff.

A portable medical device comprises a medical measuring apparatus and an elastic mounting portion. The medical measuring apparatus is adapted to monitor a subject's physical state and has a body and a sensor. The body has a mounting surface and a mounting mechanism. The mounting mechanism is formed on the mounted surface. The sensor is connected to the body.

The elastic mounting portion is arched, adapted to be mounted around a subject's wrist or arm and has two edges, an attaching surface and an attaching mechanism. The two edges are opposite to each other and define a gap for the placement of a subject's wrist or arm. The attaching surface is formed between the two edges of the elastic mounting portion. The attaching mechanism is securely attached to the attaching surface and detachably engages the mounting mechanism of the body of the medical measuring apparatus.

The medical measuring apparatus of the portable medical device in accordance with the present invention can be detachably mounted around a subject's body by the elastic mounting portion and since the elastic mounting portion is flexible, the gap between the two edges can distort for placement of the subject's wrist or arm. Thus the portable medical device is convenient for daily use and may be carried on a subject by simply mounting around the subject's wrist or arm using the elastic mounting portion.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
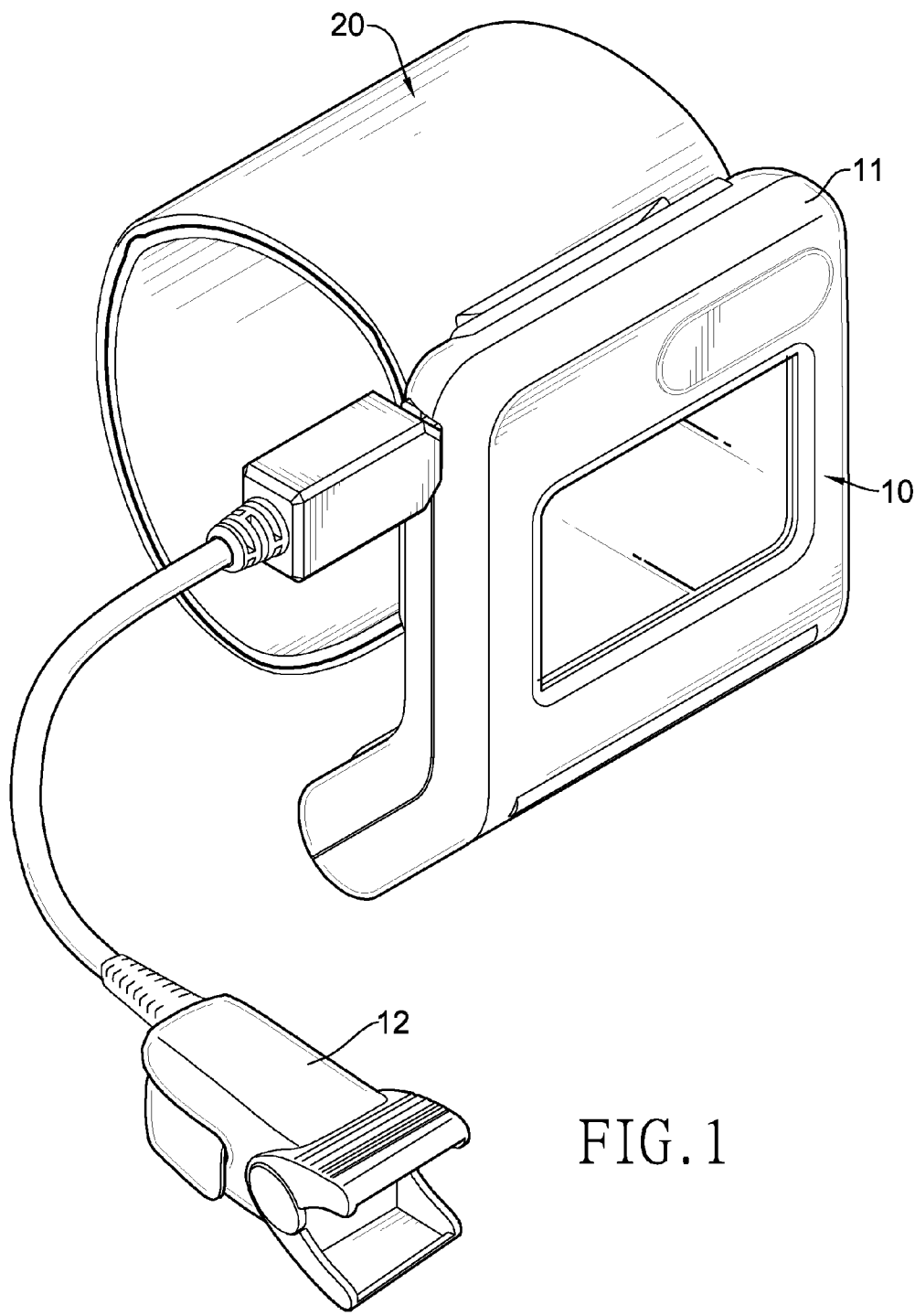
FIG. 1 is a perspective view of the portable medical device in accordance with the present invention.
Figure 2:
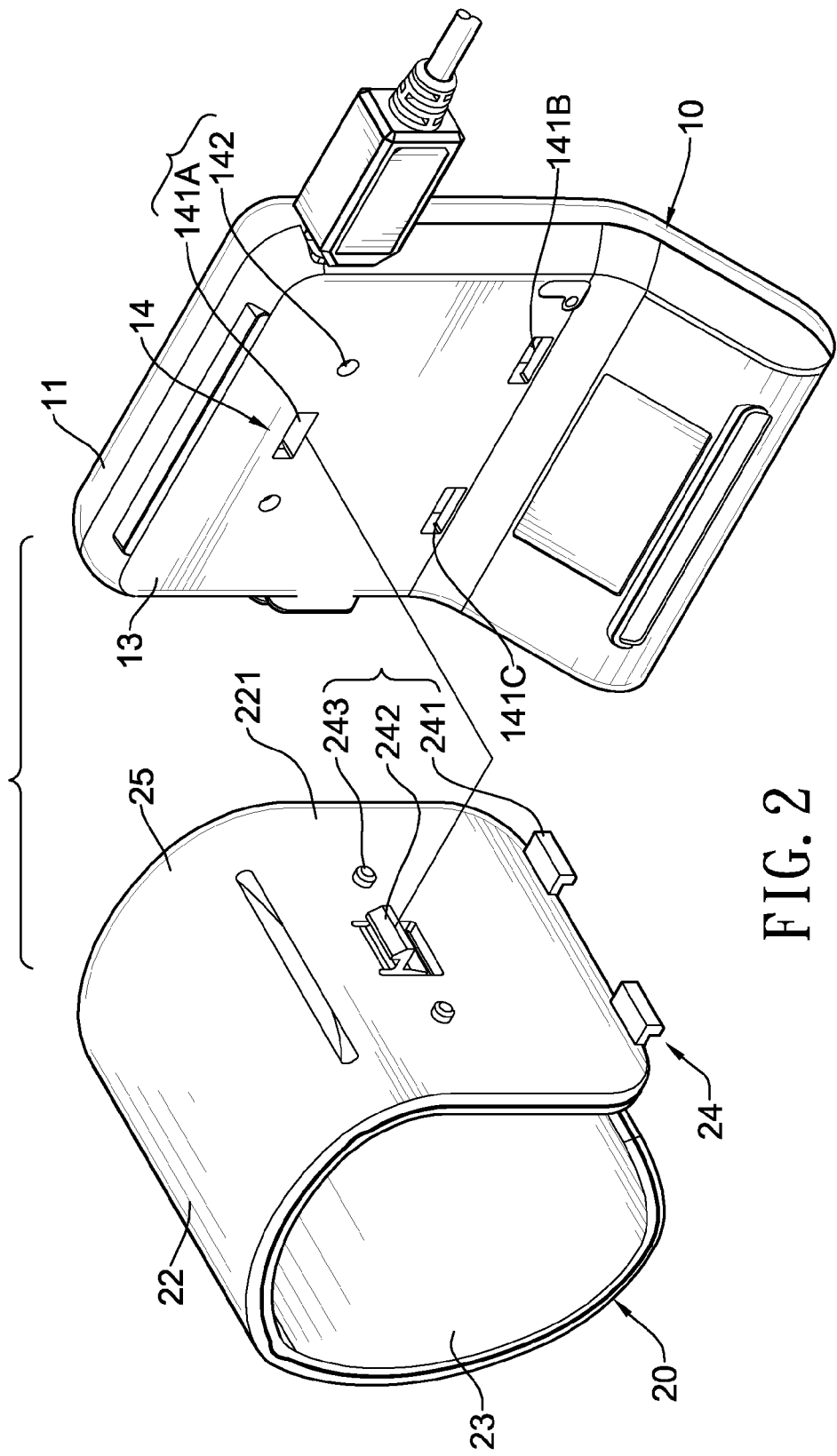
FIG. 2 is an exploded perspective view of the body of the medical measuring apparatus and elastic mounting portion of the portable medical device in FIG. 1.

With reference to FIGS. 1 and 2, a portable medical device in accordance with the present invention comprises a medical measuring apparatus (10) and an elastic mounting portion (20).

The medical measuring apparatus (10) is adapted to monitor a subject's physical state, selected from the group consisting of pulse oximeter, electronic sphygmomanometer, blood sugar meter and the like, and has a body (11) and a sensor (12). The body (11) has a mounting surface (13) and a mounting mechanism (14). The mounting mechanism (14) is formed on the mounting surface (13) and has multiple mounting holes (141A)(141B)(141C) and multiple positioning recesses (142). The mounting holes (141A)(141B)(141C) and the positioning recesses (142) are formed in the mounting surface (13) of the body (11). The sensor (12) is connected to the body (11) and is adapted to measuring physical parameters of a subject.

Figure 3:
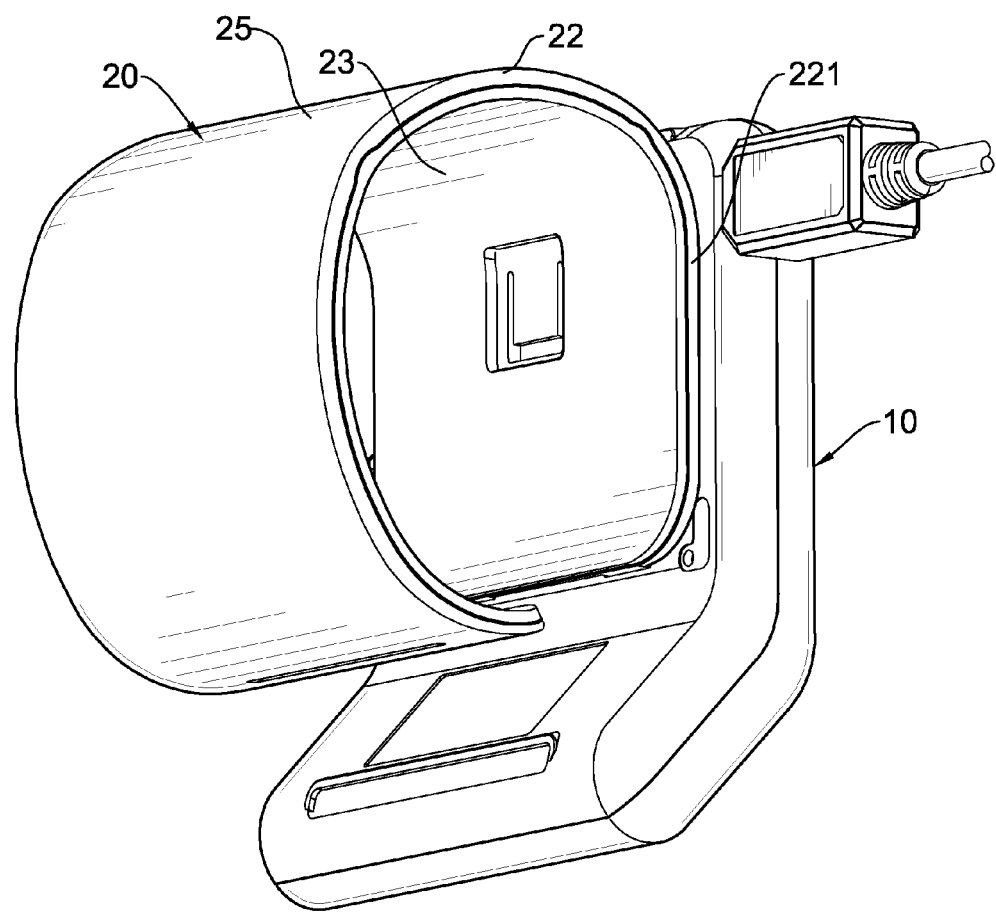
FIG. 3 is another perspective view of partial portable medical device in FIG. 1.
Figure 4:
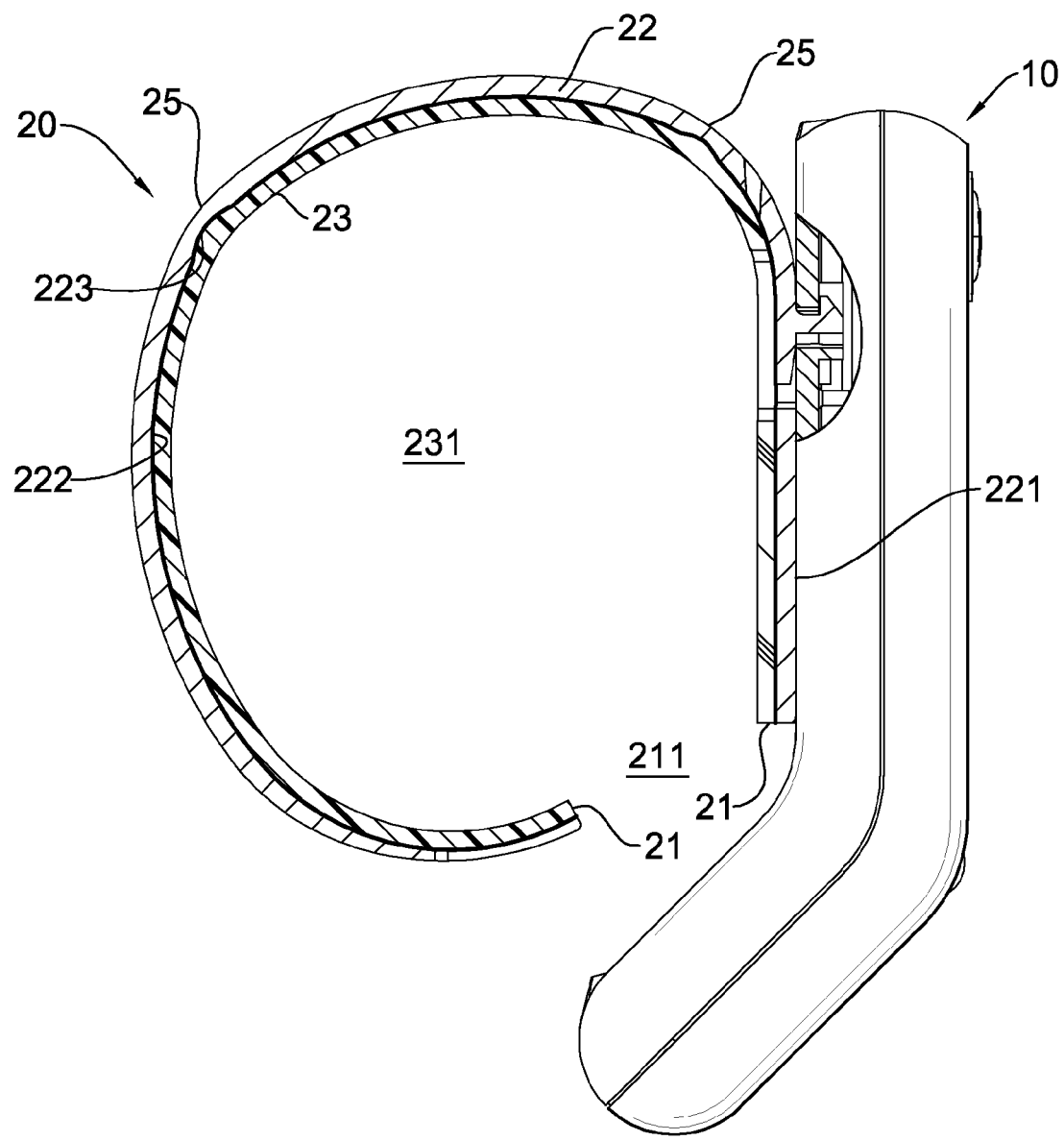
FIG. 4 is a side view of the portable medical device in FIG. 1 in partial cross section.

With reference to FIGS. 2 to 4, the elastic mounting portion (20) is connected detachably to the medical measuring apparatus (10), may be arched, is adapted to be mounted around a subject's wrist and has two edges (21), at least one turning segment (25), an outer layer (22), an inner layer (23) and an attaching mechanism (24). The edges (21) are opposite to each other. A gap (211) is defined between the edges (21) for placement of a subject's wrist or arm between the mounting portion (20) via the gap (211). The turning segment (25) is between the two edges (21) and may be formed at a right angle. The outer layer (22) is elastic, made of plastic, extends between the two edges (21) across the turning segment (25) and has an attaching surface (221) and an inner surface (222). The attaching surface (221) is formed between the two edges (21). The inner surface (222) is opposite to the attaching surface (221) and has at least one concavity (223). The concavity (223) is formed on the inner surface (222) and corresponds to a turning segment (25) of the elastic mounting portion (20). The inner layer (23) is elastic, made of rubber, extends between the two edges (21), is securely attached to the inner surface (222) of the outer layer (22) and defines a through hole (231) for accommodating a subject's wrist. The through hole (231) communicates with the gap (211) between the edges (21).

Figure 5:
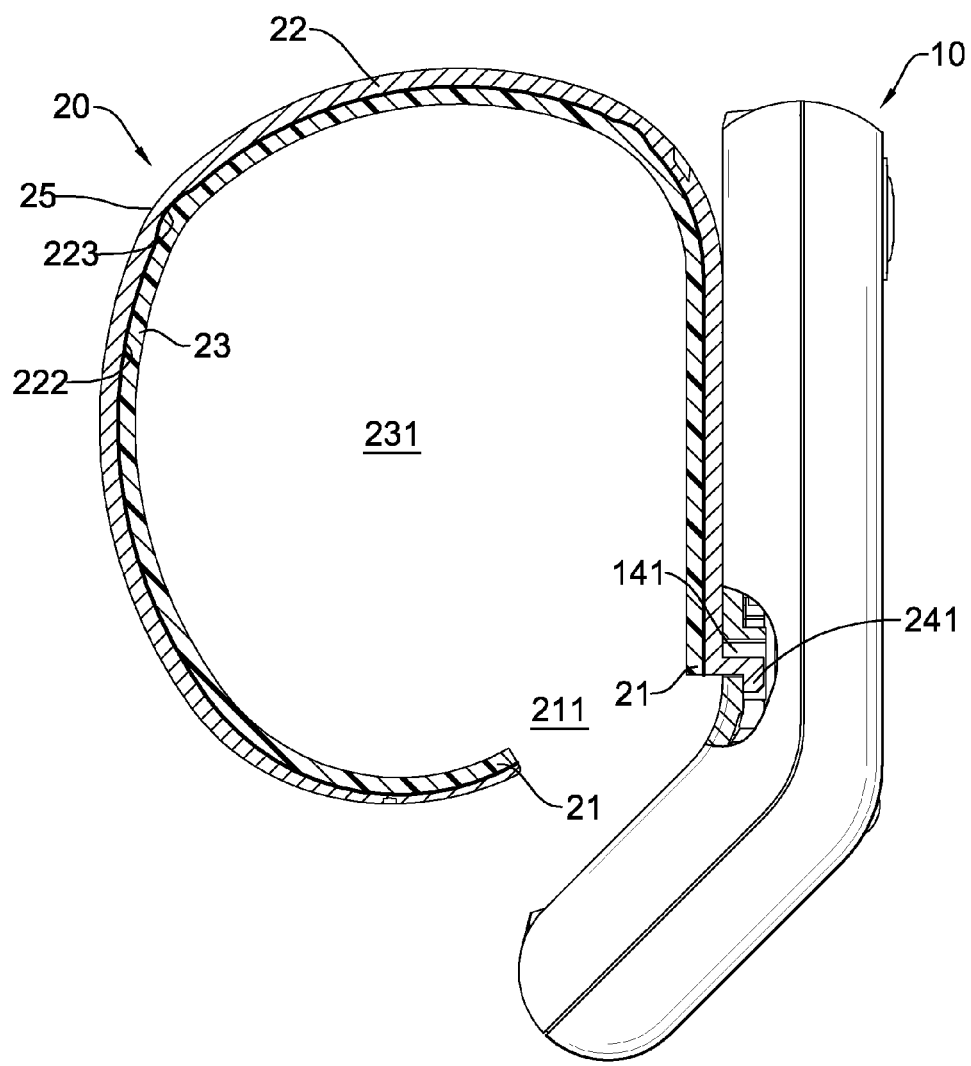
FIG. 5 is another side view of the portable medical device in FIG. 1 in partial cross section.

The attaching mechanism (24) is attached to the attaching surface (221) of the outer layer (22), detachably engages the mounting mechanism (14) of the body (11) of the medical measuring apparatus (10) and has at least one first hook (241), at least one second hook (242) and multiple positioning projections (243). As shown in FIG. 5, the at least one first hook (241) is formed at the attaching surface (221) of the outer layer (22) of the elastic mounting portion (20) and selectively engages a corresponding mounting hole (141A). As shown in FIGS. 3 and 4, the at least one second hook (242) is formed in the attaching surface (221) of the outer layer (22), selectively retracts into the inner layer (23) and selectively engages a corresponding mounting hole (141B)(141C). End edges of the first and second hooks (241, 242) respectively extend toward opposite directions. As shown in FIG. 2, each positioning projection (243) is formed on the attaching surface (221) of the outer layer (22) of the elastic mounting portion (20) and engages a corresponding positioning recess (15).

In a preferred embodiment of the present invention, the medical measuring apparatus (10) is a pulse oximeter; and the sensor (12) is adapted to be placed on a thin part of the patient's anatomy, usually a fingertip or earlobe, or in the case of a neonate, across a foot, and has a light unit emitting light at both red and infrared wavelengths to pass from one side to the other. Changed absorbance of each light at each of the two wavelengths is measured, allowing determination of the absorbances due to pulsing arterial blood alone.

In a preferred embodiment of the present invention, a thickness of the outer layer (22) corresponding to the concavity (223) of the inner surface (222) of the outer layer (22), which corresponds to the turning segment (25) of the elastic mounting portion (20), is smaller than that of other positions of the outer layer (22).

The medical measuring apparatus (10) is detachably mounted around a subject's body by the elastic mounting portion (20), since the elastic mounting portion (20) is flexible, the gap (211) between the two edges (21) of the elastic mounting portion can distort for placement of the subject's wrist or arm. The concavity (223) of the outer layer (22) of the elastic mounting portion (20) allows reduction of rigidity and increase in flexibility of the outer layer (22) to prevent stress breakage of the elastic mounting portion (20).

Furthermore, the engagement between the mounting mechanism (14) and the attaching mechanism (24) facilitates assembly of the medical measuring apparatus (10) and the elastic mounting portion (20). Since the end edges of the first and second hooks (241, 242) extend toward opposite directions, the elastic mounting portion (20) is steadily attached to the medical measuring apparatus (10) by the first hook (241) and the second hook (242). As shown in FIG. 4, for easily removing the second hook (242) from the corresponding mounting hole (141A), the second hook (242) can be retracted into the inner layer (23) of the elastic mounting portion (20).

Moreover, the inner layer (23) of the elastic mounting portion (20) is made of rubber with an appropriate adhesion to attach to the subject's wrist or arm and avoid accidental removal.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A portable medical device, comprising:
 a medical measuring apparatus adapted to monitor a subject's physical state, and having:
  a body, having
   a mounting surface; and
   a mounting mechanism formed on the mounting surface; and
  a sensor connected to the body and
 an elastic mounting portion connected to the medical measuring apparatus, adapted to be mounted around a subject's wrist or arm, and having:
  two edges opposite to each other and defining a gap for placement of a subject's wrist or arm via the gap;
  an attaching surface formed between the two edges;
  an attaching mechanism mounted on the attaching surface and detachably engaging the mounting mechanism of the body of the medical measuring apparatus;
  an elastic outer layer, extending between the two edges and having the attaching surface and an inner surface opposite to the attaching surface; and
  an elastic inner layer, extending between the two edges and securely attached to the inner surface of the outer layer.

2. The portable medical device of claim 1, wherein
 the elastic mounting portion further has a turning segment;
 the outer layer extends across the turning segment; and
 the inner surface of the outer layer has a concavity formed on the inner surface corresponding to the turning segment.

3. The portable medical device of claim 1, wherein
 the mounting mechanism has
  multiple mounting holes formed on the mounting surface of the body; and
 the attaching mechanism has
  at least one first hook formed at the attaching surface of the outer layer, and selectively engaging one of the mounting holes and having an end edge; and
  at least one second hook formed on the attaching surface of the outer layer, and selectively engaging one of the mounting holes and having an end edge; and
 the end edges of the first second hooks respectively extend toward opposite directions.

4. The portable medical device of claim 3, wherein the at least one second hook selectively retracts into the inner layer.

5. The portable medical device of claim 3, wherein
 the mounting mechanism further has
  multiple positioning recesses formed on the mounting surface of the body; and
 the attaching mechanism further has
  multiple positioning portions formed on the attaching surface of the outer layer of the elastic mounting portion and respectively engaging the positioning recesses.

6. The portable medical device of claim 1, wherein the medical measuring apparatus is selected from the group consisting of pulse oximeter, electronic sphygmomanometer and blood sugar meter.

7. The portable medical device of claim 2, wherein the medical measuring apparatus is selected from the group consisting of pulse oximeter, electronic sphygmomanometer and blood sugar meter.

8. The portable medical device of claim 1, wherein the outer layer is made of plastic; and the second layer is made of rubber.

9. The portable medical device of claim 2, wherein the outer layer is made of plastic; and the second layer is made of rubber.

10. The portable medical device of claim 3, wherein the outer layer is made of plastic; and the second layer is made of rubber.

* * * * *